US00PP12292P2

(12) United States Plant Patent
Stemkens

(10) Patent No.: US PP12,292 P2
(45) Date of Patent: Dec. 18, 2001

(54) VERBENA PLANT NAMED 'WYNENA'

(75) Inventor: Henricus G. W. Stemkens, Hoorn (NL)

(73) Assignee: Syngenta Seeds B.V., Enkhuisen (NL)

( * ) Notice: Subject to any disclaimer, the term of this patent is extended or adjusted under 35 U.S.C. 154(b) by 0 days.

(21) Appl. No.: 09/615,400

(22) Filed: Jul. 13, 2000

(51) Int. Cl.[7] ..... A01H 5/00
(52) U.S. Cl. ..... Plt./308
(58) Field of Search ..... Plt./308

(56) References Cited

PUBLICATIONS

UPOV–ROM GTITM Computer Database 2001/01, Feb. 6, 2001, GTI Jouve Retrieval Software, Citation for 'Wynena'.*

* cited by examiner

*Primary Examiner*—Bruce R. Campell
*Assistant Examiner*—June Hwu
(74) *Attorney, Agent, or Firm*—Bruce Vrana

(57) ABSTRACT

A new Verbena plant particularly distinguished by its burgundy flower, early flowering, no seed set, and with a spreading habit.

1 Drawing Sheet

BACKGROUND OF THE NEW PLANT

The present invention comprises a new distinct cultivar of Verbena, botanically known as *Verbena×hybrida*. The new cultivar is propagated from cuttings resulting from the cross of 'U1023' and 'U1021'. 'U1023' is a pink flowering Verbena having a semi-erect habit. 'U1023' is commercially available and is known by the name 'Morena'. 'U1021' a violet flowering Verbena having a spreading habit. 'U1021' is not commercially available and is not known by any synonyms. 'U1021' has not been patented. U1023 is patented as 'Morena' (U.S. Plant Pat. No. 11,231). As a result of this cross the present cultivar was created in 1996 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new Verbena plant is an annual in most climatical zones in the US, only in zones 9 and 10 it is a perennial plant.

DESCRIPTION OF THE DRAWING

This new Verbena plant is illustrated by the accompanying photographic drawings which show blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on 14 weeks old plants, blossomed under natural light in a greenhouse. Color readings were taken in the greenhouse under ambient light. Color references are primarily to the R.H.S. Color Chart of The Royal Horticultural Society of London.

Differences between the new variety 'Wynena', its parents and a similar cultivar

| Character | 'Wynena' | 'U1023' | 'U1021' | 'Tapien blue' |
|---|---|---|---|---|
| Flower color | 87A | 38D | 90A | 95B |
| Seed set | No | No | Yes | Yes |
| Flower size | Large | Large | Large | Small |

The plant:

*Classification.*—Botanical: *Verbena×hybrida.*

*Parentage.*—Female parent: A seedling named 'U1023' is one of our seedling from our U-generation of plants bred in 1991. Pollen parent: A seedling named 'U1021' is one of our seedlings from our U-generation of plants bred in 1991.

*Growth habit.*—Spreading.

*Plant height.*—15–25 cm.

*Spreading area of plant.*—70–90 cm.

*Growth rate.*—Vigorous.

*Strength.*—Very good.

*Branching character.*—Freely branching and lateral branching at every node.

*Blooming period.*—From April until November.

The stem:

*Diameter.*—1.5–2.0 mm.

*Shape.*—Tetragonal.

*Color.*—Light green 137C.

*Anthocyan pigmentation.*—Absent.

*Length of internode.*—20–40 mm, depending on the light where the plant is propagated.

*Pubescence.*—Slightly pubescent.

The foliage:

*Phyllotaxis.*—Opposite.

*Shape of blade.*—Broadly ovate, with very deep incisions.

*Venation.*—Pinnate on upper and lower surface.

*Leaf margin.*—Lacerate to Laciniate.

*Leaf base.*—Shortly attenuate.

*Leaf apex.*—Acuminate.

*Texture.*—Upper side: Slightly pubescent. Lower side: Slightly pubescent.

*Length.*—25–40 mm.
*Width.*—22–38 mm.
*Depth of incision.*—10–20 mm. *Color.*—Upper side: Medium green 141A. Lower side: Light green 143A.
*Length of petiole.*—5–15 mm.
*Color of petiole.*—Light green 143A.
*Petiole surface texture.*—Slightly pubescent.

The bud:
*Peduncle length.*—30–60 mm, depending on season.
*Size.—Diameter* 2 mm. Length: 8–12 mm.
*Shape.*—Elongated and conical.
*Color.*—Medium green 141A.
*Color when calyx begins to unfold.*—83B.
*Sepals.*—Color: Green 137D. Form: Upright. Number: 5, fused. Size: 7 mm. Shape: Elongated. Surface Texture: Slightly pubescent.

The flower:
*Direction.*—Ascending.
*Diameter.*—18–24 mm.
*Corolla tube length.*—16–18 mm.
*Borne.*—In a cluster.
*Form.*—Salverform; sessile on terminal spikes.
*Cluster.*—Spike
*Color.*—Burgundy 87A, towards base darker 83B.
*Eye.*—Absent.
*No. of petals.*—Gametopetalous, five lobed.
*Overlapping of petals.*—Separate.
*Shape of the petals.*—Each petal is heart shaped at the apex and grown together at the base.
*Petal surface texture.*—Smooth.
*Size of the petal.*—Length: 6–8 mm. Width: 5–7 mm.
*Spike.*—Length: 30–50 mm. Diameter 40–50 mm.
*Calyx.*—Length of 10–12 mm.
*Anthocyan pigmentation of calyx limb.*—Absent.
*No. of flowers per spike.*—30–40.
*Fragrance.*—No fragrance.
*Lastingness of the bloom.*—New florets continue to open in one spike over a period of 20 days.

Reproductive organs: One pistil and four stamens in pairs; color for both is yellow green 150C. The pistil size is 15–17 mm in length. Pollen is present with a color of yellow 5D. The filaments and anthers are fused to the corolla. The anthers are enclosed and not a prominent feature of the flower. 'Wynena' doesn't freely set seed.

Roots:
*Type of roots.*—Fibrous, Roots start to grow on every part of the stem that contacts the soil, so not only at the nodes.

Physiological and ecological characteristics: Good tolerance to heat and cold. Strong resistance to pests and diseases; particularly powdery mildew.

What is claimed is:

1. A new and distinct variety of Verbena plant, substantially as herein illustrated and described, characterized particularly as to novelty by larger burgundy flowers than other Verbena plants, which appear earlier on the plant, and a growing habit that is spreading and hanging.

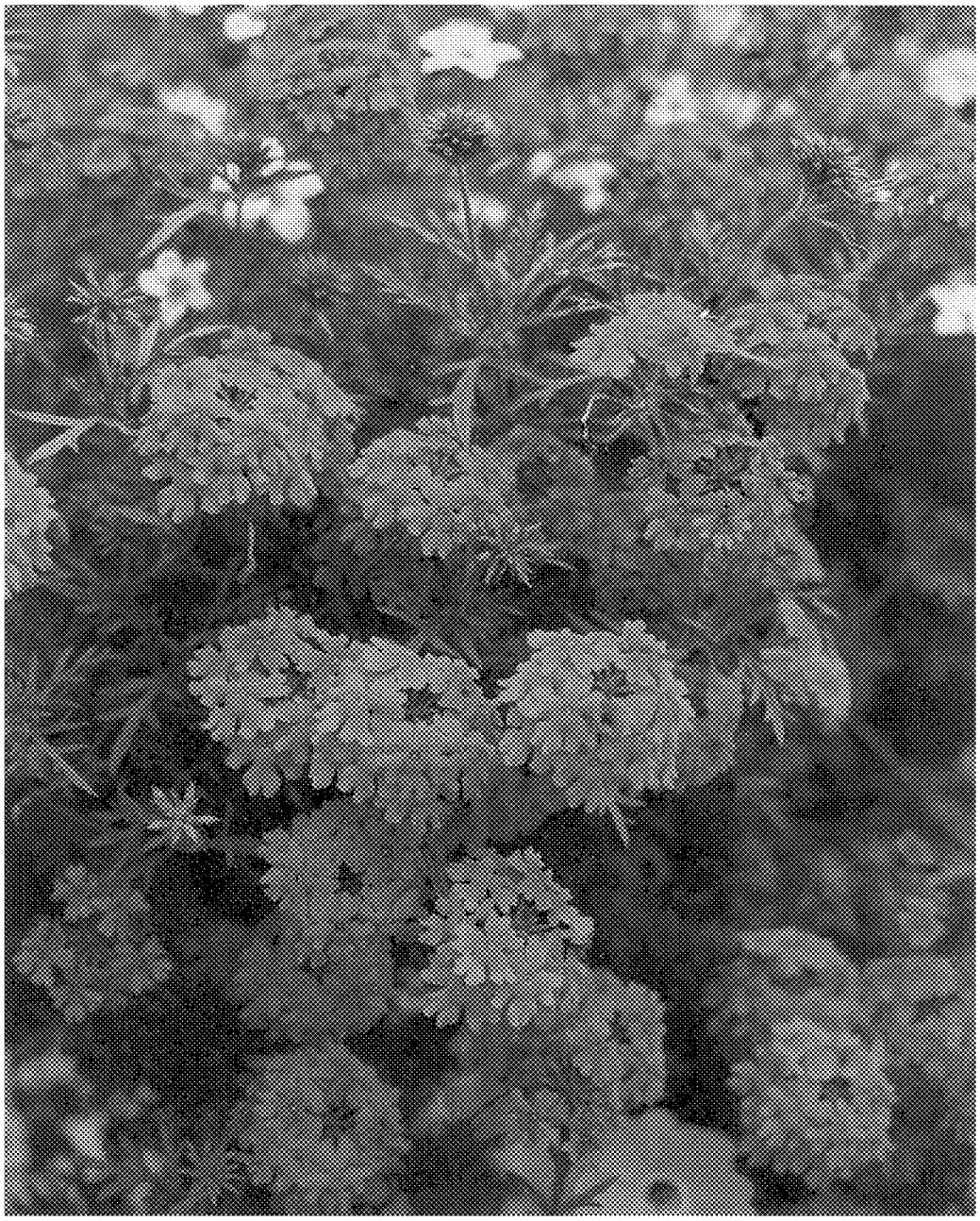

* * * * *